United States Patent [19]

Goedecke et al.

[11] 4,344,897

[45] Aug. 17, 1982

[54] PROCESS FOR THE PREPARATION OF PERCARBOXYLIC ACID SOLUTIONS

[75] Inventors: Ralf Goedecke; Willi Hofen, both of Rodenbach; Hermann Seifert; Gerd Siekmann, both of Cologne, all of Fed. Rep. of Germany

[73] Assignee: Bayer Aktiengesellschaft, Leverkusen, Fed. Rep. of Germany

[21] Appl. No.: 102,817

[22] Filed: Dec. 13, 1979

[30] Foreign Application Priority Data

Dec. 29, 1978 [DE] Fed. Rep. of Germany ....... 2856665

[51] Int. Cl.³ ...................... C07C 179/00; B01D 3/36
[52] U.S. Cl. .................................. 260/502 R; 203/15; 203/43; 203/60; 203/63; 203/67; 203/68; 203/69; 203/70
[58] Field of Search ............... 260/502 R; 203/15, 43, 203/69, 60, 63, 68, 70

[56] References Cited

U.S. PATENT DOCUMENTS

| | | | |
|---|---|---|---|
| 4,059,619 | 11/1977 | Prescher et al. | 260/502 R |
| 4,071,541 | 1/1978 | Hildon | 260/502 R |
| 4,113,747 | 9/1978 | Prescher et al. | 260/502 R |
| 4,137,242 | 1/1979 | Prescher et al. | 260/502 R |
| 4,142,058 | 2/1979 | Matsumura et al. | 203/43 |
| 4,168,274 | 9/1979 | Hildon et al. | 260/502 R |

FOREIGN PATENT DOCUMENTS

2262970 7/1974 Fed. Rep. of Germany ... 260/502 R

*Primary Examiner*—Wilbur L. Bascomb, Jr.
*Attorney, Agent, or Firm*—Sprung, Horn, Kramer & Woods

[57] ABSTRACT

In a process for the continuous preparation of pure organic solutions of percarboxylic acids having 2 to 5 carbon atoms, by (a) contacting aqueous hydrogen peroxide with a carboxylic acid containing 2 to 5 carbon atoms in the presence of an acid catalyst at a feed molar ratio of $H_2O_2$ to carboxylic acid of 0.5:1 to 30:1,

(b) isolating an extract essentially containing the percarboxylic acid and possibly the corresponding carboxylic acid not converted in stage (a), by extracting the reaction mixture obtained according to stage (a) with an organic solvent, (c) treating the extract with water or an aqueous solution in an extraction unit provided with one to ten theoretical separation stages and (d) dehydrating the solution of the percarboxylic acid and organic solvent obtained according to (c), by azeotropic distillation, the improvement wherein the organic phase of the top product of the azeotropic distillation, obtained during the dehydration according to (d), is entirely or partially recycled to stage (c) and/or entirely or partially recycled to stage (b).

15 Claims, 4 Drawing Figures

PROCESS FOR THE PREPARATION OF PERCARBOXYLIC ACID SOLUTIONS

The present invention relates to a continuous process for the industrial preparation of pure percarboxylic acid solutions in organic solvents. In particular, the present invention relates to a process for the preparation of organic solutions of percarboxylic acids having 2 to 5 carbon atoms, which solutions are free, or substantially free, from water, hydrogen peroxide and strong acid.

Percarboxylic acids are increasingly gaining importance as oxidizing agents which can be used on an industrial scale. For example, percarboxylic acids can be used to convert olefins into epoxides and cyclic ketones into lactones (compare D. Swern, Organic Peroxides, Vol. II, pages 355–502, John Wiley-Interscience 1971, and Houben-Weyl, Methoden der Organischen Chemie (Methods of Organic Chemistry), Volume VI/2, pages 707–711, Georg Thieme Verlag 1963).

Aqueous percarboxylic acid solutions which are easily obtainable, for example by the process of German Patent Specification No. 1,165,576, are however, because of the presence of water, not advantageous for carrying out such oxidation reactions, since the water very rapidly reacts further with the desired oxidation products, namely the epoxides or the lactones, and this can lead to considerable formation of by-products.

Strong acids, or free hydrogen peroxide present, exert the same adverse effect on the yield of oxidation products, and in particular traces of mineral acids, which are introduced into the reaction mixture together with the percarboxylic acid solutions, can, if water is present simultaneously, make it completely doubtful whether the reaction, yielding, for example, epoxides or lactones, can be carried out successfully, since the formation of by-products becomes the main reaction (compare Methodicum Chimicum, Volume 5, page 170, Georg Thieme Verlag (1975), as well as Houben-Weyl, Volume VI/2, page 708, Georg Thieme Verlag (1963) and J. Amer. Chem. Soc. 80, 4079 (1958)).

Anhydrous or substantially anhydrous solutions of percarboxylic acids in organic solvents can, as a study of the prior art shows, be obtained in very diverse ways.

The method of converting aldehydes into percarboxylic acids by oxidation in an organic solvent, for example in accordance with the process of German Auslegeschrift No. 1,043,315 (U.S. Pat. No. 2,804,473) has the disadvantage that in the course of carrying out the process highly explosive intermediate products are formed (compare Ullmanns Enzyklopädie der techn. Chemie (Ullmann's Encyclopedia of Industrial Chemistry), New Processes (supplementary volume) page 181, (1970)) and that the carboxylic acids corresponding to the aldehydes are obtained as by-products after the oxidation reaction of the percarboxylic acid has been carried out, which largely excludes use of such processes on a substantial scale, both for safety reasons and for economic reasons. The carboxylic acid corresponding to the aldehyde cannot be recycled to the process. Furthermore, the organic solutions of percarboxylic acids obtained by the aldehyde oxidation process contain impurities resulting from more extensive oxidative degradation of the aldehyde, taking place simultaneously with the process of preparation.

Furthermore, anhydrous or substantially anhydrous organic solutions of percarboxylic acids can be prepared by discontinuous or continuous extraction and azeotropic subsequent dehydration of the resulting extracts, or alternatively merely by azeotropic dehydration of the aqueous percarboxylic acid solutions, a part of the organic solvent used being employed for diluting the percarboxylic acids, as proposed in Belgian Patent Specifications Nos. 788,727, 788,729 and especially 788,728. The solutions to be extracted are prepared by reacting $H_2O_2$ with carboxylic acids in the presence of acid catalysts. The processes described have a high energy consumption because, in every case where an aqueous percarboxylic acid solution is prepared, water and, additionally, the percarboxylic acid must be distilled. This measure entails a high energy consumption and, furthermore, expensive safety precautions because of exposing the percarboxylic acids to heat. In addition, because of the corrosive properties of peracids undergoing distillation, special materials of construction must be employed, which also substantially rule out large-scale industrial application of these processes.

If pure organic solutions of peracids are to be obtained, the water contained in the aqueous percarboxylic acids obtained by distillation must furthermore again be removed by azeotropic distillation, which demands additional measures (compare Ullmann, Enzyklopädie der Technischen Chemie (Encyclopedia of Industrial Chemistry), supplementary volume 1970, New Processes, page 181 et seq., and D. Swern, Organic Peroxides, Vol. I, 1970, page 313 et seq.).

Further, it is known that organic percarboxylic acid solutions can be obtained if the percarboxylic acid is extracted with a water-immiscible organic solvent from a previously equilibrated mixture resulting from the acid-catalyzed reaction Carboxylic acid + $H_2O_2$ ⇌ Percarboxylic acid + $H_2O$.

In this process, the extraction for obtaining the organic solutions of percarboxylic acids is carried out in a single stage, as described in German Offenlegungsschrift No. 1,618,625, or in several stages, as disclosed in German Auslegeschrift No. 1,048,569. The catalyst used to set up the abovementioned equilibrium is, in industrial operation, in most cases sulphuric acid, as described in German Patent Specification No. 2,262,970, German Patent Specification No. 2,602,776 and German Auslegeschrift No. 2,519,289. The extraction itself is carried out in counter-current, in most cases in extraction columns provided with a great variety of internal fitments.

In all these recent processes for the preparation of organic solutions of percarboxylic acids—the so-called extraction processes—in which aqueous mixtures consisting of percarboxylic acid, acid catalyst and hydrogen peroxide are extracted with organic solvents, extracts are obtained which still contain water, $H_2O_2$ and strong mineral acid—in some cases in considerable amounts. The concentrations at which these impurities are present in the organic solution of the percarboxylic acid depend essentially on two parameters. On the one hand, the polarity of the organic solvent used plays a role and on the other hand the extraction conditions, especially the temperature under which the extraction is carried out, and the concentration of strong acid present in the aqueous phase, exert an influence.

It is understandable that the quality of these percarboxylic acid solutions obtained by extraction is necessarily completely inadequate, for example, for the reaction with olefins, giving olefin oxides. Hence, additional technological steps have been proposed for purifying such organic percarboxylic acid solutions.

German Patent Specification No. 2,262,970, 3rd column, lines 26–32, proposes to treat the percarboxylic acid solution, in a continuously operated post-extraction, with water or an aqueous solution in counter-current, in order, in particular, to recover the hydrogen peroxide, that is to say, to purify the extract in the sense of removing the $H_2O_2$ contained therein. The water content of the organic percarboxylic acid solutions washed in this way is subsequently between 1 and 2% by weight.

According to the process of German Offenlegungsschrift No. 2,602,776, the after-treatment of the crude percarboxylic acid extract is carried out with sulphuric aid, the extraction system used to obtain the percarboxylic acid solution. As a result of the use of aqueous sulphuric acid for the post-wash, the washed percarboxylic acid solution must necessarily contain not only water but also small proportions of this strong mineral acid. The contents of these two impurities are not shown precisely in the said German Offenlegungsschrift No. 2,602,776. However, for example, water contents of 2% by weight and sulphuric acid contents of only 500 ppm in the organic solution of the percarboxylic acid are entirely realistic. Such concentrations of these impurities however result in substantial formation of by-products in the preparation of epoxides, such as, for example, propylene oxide, in particular also during the subsequently necessitated distillative working-up of the epoxide-containing reaction mixture, so that the economics of a process employing this peracid solution become questionable.

The said disadvantages with respect to the content of strong acid and of water in the organic percarboxylic acid solution are substantially avoided in the process of German Offenlegungsschrift No. 2,519,298. This Offenlegungsschrift describes a process for the preparation of propylene oxide wherein the oxidizing agent employed is preferentially a solution of perpropionic acid in benzene, which has been washed with water or with an aqueous solution in order to remove strong acid and hydrogen peroxide and has subsequently been subjected to an azeotropic distillation in order to remove the water introduced into the benzene solution by the washing process. The dissolved water, as well as the water entrained with the organic phase during the post-wash, is removed, in this process step, as a water-benzene azeotrope at the top of a distillation unit, and the benzene obtained as the light phase after condensing the top vapors and separating the phases is in its entirety charged into the distillation column as reflux.

This process requires a substantial expenditure of energy since considerable amounts of water must be distilled off and in addition high reflux ratios are necessary. Furthermore, the results achievable by this process with respect to the content of free hydrogen peroxide in the organic solution are as yet not to be regarded as satisfactory.

In contrast, it has now been found, surprisingly, that pure organic solutions of percarboxylic acids having 2 to 5 carbon atoms can be prepared continuously in a technically and economically advantageous manner by (a) reaction of aqueous hydrogen peroxide with carboxylic acids containing 2 to 5 carbon atoms in the presence of acid catalysts at a feed molar ratio of $H_2O_2$ to carboxylic acid of 0.5:1 to 30:1, (b) isolating an extract essentially containing the percarboxylic acid and possibly the corresponding carboxylic acid not converted in stage (a), by extracting the reaction mixture obtained according to stage (a) with an organic solvent, (c) treating the extract with water or an aqueous solution in an extraction unit provided with one to ten theoretical separation stages and (d) dehydrating the organic solution of the percarboxylic acid, obtained according to (c), if necessary after adding a further organic solvent, by azeotropic distillation, if the organic phase of the top product of the azeotropic distillation, obtained during the dehydration according to (d), is entirely or partially recycled to stage (c) and/or entirely or partially recycled to stage (b). In doing so, the entire amount, or a part, of the organic phase to be recycled to stage (c) can preferentially be fed to the extraction unit, employed for step (c), before the first theoretical separation stage, or be fed to the said unit at a point after the first, and before the last, theoretical separation stage.

However, it is also possible to recycle the entire amount, or a part, of the organic phase obtained from stage (d) to stage (b). Equally, one can feed the entire amount of the organic phase obtained in carrying out stage (d) or parts thereof, both to stage (c) and to stage (b).

Suitable organic solvents for the process according to the invention are all compounds which are inert towards the percarboxylic acid and which have a boiling point, under normal pressure, of about 30° C. to about 140° C. Furthermore, the organic solvents should have a very low solubility in water or aqueous sulphuric acid and should, in addition, be capable of forming an azeotrope with water, the boiling point of which is at least 10° C. below the boiling point of the percarboxylic acid. It should be noted that, of course, the organic phase from (d) to be recycled, according to the invention, to stage (b) and/or stage (c) essentially consists of organic solvent conforming to the criteria mentioned.

These solvents can be of very diverse chemical nature. For example, the following prove suitable: aromatic hydrocarbons which contain 6 to 10 carbon atoms, aliphatic or cycloaliphatic hydrocarbons which contain 5 to 12 carbon atoms, chlorinated hydrocarbons which contain 1 to 10 carbon atoms and 1 to 4 chlorine atoms, and esters of carboxylic acids, containing 1 to 5 carbon atoms, with straight-chain or branched alcohols in which there are 1 to 8 carbon atoms present in the molecule, as well as ethers which contain 2 to 10 carbon atoms.

Preferably, chlorinated hydrocarbons which are derived from alkanes or alkenes are used, such as, for example, methylene chloride, carbon tetrachloride, dichloroethane, 1,2-dichloropropane, trichloroethylene and tetrachloroethylene, or aromatic hydrocarbons, such as benzene, toluene or chlorobenzene, or ethers, such as diisopropyl ether, or esters, such as methyl acetate, ethyl acetate, n-propyl acetate, isopropyl acetate or n-butyl acetate. However, it is also possible, and in some cases even advantageous, to use mixtures of these solvents.

The acid-catalysed reaction of $H_2O_2$ with the carboxylic acid, according to stage (a), can be carried out in a manner which is as such known, for example in accordance with the processes described in German Pat. No. 2,262,970, or German Offenlegungsschrift No.

2,519,298 or German Auslegeschrift No. 2,519,289 or German Offenlegungsschrift No. 2,602,776. Equally, process steps (b), (c) and (d) are carried out in a manner which is as such known, for example in accordance with the processes described in German Pat. No. 2,262,970, German Offenlegungsschrift No. 2,519,298 or German Auslegeschrift No. 2,519,289.

Any apparatus suitable for carrying out extractions can be used for process step (c). In general, extraction columns which operate on the counter-current principle, or mixer-separator batteries, which can be operated partly in counter-current and partly in cross-current, are used. One can also use different, combined extractors, or centrifugal extraction machines. Advantageously, 1 to 18% by volume, relative to the organic extract, of water or aqueous solution are used. Preferably, 3 to 6% by volume of water are used. Instead of pure water, it is also possible to use an aqueous solution containing at least 90% by weight of water, which is substantially free from hydrogen peroxide and from mineral acid. It is advantageous to use an aqueous phase obtained in the course of the process. For example, the aqueous phase from the azeotropic distillation according to (d) is suitable.

Customary columns, such as, for example, known tray columns or packed columns, are suitable for stage (d), the dehydration by azeotropic distillation. Advantageously, both the column body of this distillation unit and the internal fitments, as well as the evaporating unit and the condensation system, are made from stainless steels.

BRIEF DESCRIPTION OF DRAWINGS

Referring to the appended drawings.

A general embodiment of the process according to the invention will be described below in relation to the flow scheme shown in FIG. 1:

The reaction according to step (a) is carried out in a manner which is in itself known in the reaction system (3). A mixture of aqueous $H_2O_2$ and acid catalyst, such as, for example, sulphuric acid, is introduced via line (1), whilst the carboxylic acid is introduced into the reaction system via (2). The aqueous reaction mixture containing the percarboxylic acid is fed via line (4) to the extraction system (5), where process step (b) is carried out. It should be emphasized at this point that the reaction system (3) can also be integrated into the extraction system (5).

The organic solvent passes via (6) into the unit (5). The extract obtained according to stage (b) is drawn off via line (7). This extract contains the percarboxylic acid, the carboxylic acid corresponding to the percarboxylic acid, unless the carboxylic acid has been completely converted in stage (a), and certain amounts of water, hydrogen peroxide and acid catalyst. The removal of these three compounds is achieved by the two next process steps, (c) and (d), which are carried out in apparatuses (8) and (9).

The treatment of the extract obtained according to (b), with water or an aqueous solution is carried out in an extraction unit (8), which is so designed that 10 theoretical separation stages can be realized therein, as symbolised by the trays shown in the drawing. The washed extract leaves the apparatus (8) via line (10) and is then fed to the distillation unit (9), where a part of the organic solvent, together with the water present in the stream (10)—the organic solution of the percarboxylic acid—is taken off at the top. The mixture of organic solvent and water is condensed in the cooler (11) and is separated in the separator (12) into an organic phase, which essentially contains the organic solvent, and an aqueous phase. The organic solvent obtained in (12) is, for example, recycled via line (13) and (13a) to the extraction unit (8), upstream of the first theoretical separation stage.

It is however also possible, and advantageous in carrying out the process in practice, to recycle a small proportion of the organic solvent arising in (12), to the column (9), as reflux, via (14). In general, in the process according to the invention, the proportion which passes via (14) to (9) is less than the proportion which is fed via line (13) and (13a) or (15) to (8), or via (13) and (22) to (5). The ratio of the stream (14) to the stream (13) is, for example, 1:10. Preferably, this ratio is in the range from 1:5 to 1:3, and very particularly preferentially in the range from 1:3 to 1:1.1.

The organic solvent to be recycled to the extraction unit (8), that is to say to the process stage (c), is now introduced, in its entirety, via (13) and (13a), upstream of the first theoretical stage into (8). However, it is also possible to introduce a part of the stream (13) via line (15) at a point of the extraction unit (8) which, as indicated in FIG. 1, is downstream of the first and upstream of the last theoretical stage. Equally, it is possible to introduce the entire stream (13) via line (15) at the said point. Yet a further possibility is to employ the organic solvent, which arises in (12), entirely or partially for some other use, in which case corresponding amounts of fresh organic solvent are then introduced via line (13), (13a) and/or (15) into stage (c), that is to say into the extraction unit (8), or via (13) and (22) into stage (b), that is to say into the extraction system (5).

The aqueous phase which arises in the separator (12) is also fed to unit (8), via line (16). This stream (16) can, if appropriate, be supplemented by further amounts of water or aqueous solution via line (17).

The aqueous phase which arises in carrying out stage (c) in the extraction unit (8), and which contains the washed-out acid catalyst as well as the recovered $H_2O_2$, is fed either via line (18) and (18a) to the extraction (5) or via line (18) and (19) to the reaction system (3). It is also possible to feed part of the aqueous phase leaving (8) to (5) and the remainder to (3). For example, the stream (18) can be divided up so that 40–90% of this stream are introduced into reaction system (3).

Regarding the dividing-up of the solvent, arising as the organic phase in the separator (12), into the individual streams (14), (13), (13a), (15) and (22), the following data may be given by way of example. The data relate to the process represented in FIG. 1. In the separator (12), 150 parts of ethyl acetate and 5 parts of water arise, per unit time, in the stationary state of the installation. Of this amount of ethyl acetate, 30 parts are then fed via line (14) to the column, as reflux, whilst the remaining 120 parts are taken off via line (13). 70 parts, for example, are fed to a unit (8), operating in counter-current and consisting of five mixer-separators, upstream of the first mixer, and 20 parts of ethyl acetate are fed in downstream of the third mixer-separator. The 30 parts which still remain are fed via (22) to process step (b). The extract taken off from (5) and passing to (8) in that case contains 180 parts of ethyl acetate.

In some cases it can be advantageous to feed a part of the stream (13), not to the extraction unit (8), but instead via line (22) to the extraction stage (5), in which process step (b) is carried out. In general, however, the proportion of (13) which is fed via (22) to the extraction unit (5) is low, if at the same time proportions of (13) are recycled via (13a) and/or (15) to (8). However, it is also possible to feed the entire organic phase arising in (12), or a part thereof exclusively to stage (b), that is to say to the extraction system (5), in which case the extraction (8) is not exposed to any organic solvent arising in (12). If the organic phase is being simultaneously recycled both to (8) and to (5), the ratios of the product streams are in general selected so that the amount of (22) is 5–70% of the amount which is fed via (13a) and/or (15) to (8). Preferably, the ratio is so chosen that stream (22) accounts for 10–50% of the total amount of organic phase reaching (8).

Particularly preferentially, however, the entire organic phase arising in (12), or a part thereof, is either entirely recycled to stage (c) or entirely to stage (b).

However, in such a procedure, in which the organic phase arising in (12) is fed entirely or partially both to (8) and to (5), the stream (22) is preferably introduced into the extraction unit (5) one to five theoretical separation stages downstream of the point of entry of the organic solvent introduced via (6).

The organic solvent recycled to (8) and/or (5) is in general saturated with water. In addition it may also contain small amounts of percarboxylic acid, for example 0.1 to 5% by weight, but these do not affect the execution of the process. If, however, a part or all of the organic solvent arising in (12) is recycled to process stage (b), it is advantageous if the content of percarboxylic acid in stream (13) or (22) is not more than 1.5% by weight.

Figure 1:
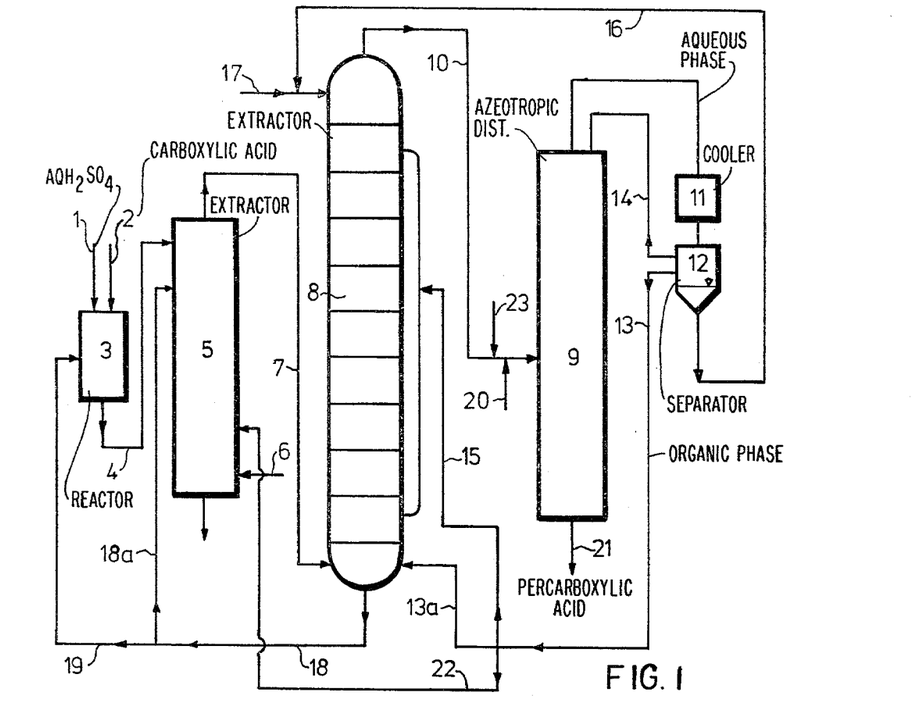
FIG. 1 is a flow diagram showing one process for preparing a percarboxylic acid solution in accordance with the present invention.

It should be mentioned at this point that the process of FIG. 1, as is readily clear to an expert, concerns a combination of percarboxylic acid and organic solvent, where the extract obtained in (8) and taken off via (10) is of lower specific gravity than the aqueous phase, containing acid catalyst, which is present in (8) and is taken off via (18). Equally, stream (7), that is to say the organic solution of the percarboxylic acid, which contains $H_2O$, $H_2O_2$ and strong acid as impurities, is of lower specific gravity than the aqueous phase arising in (5). The same is true for the conditions prevailing in the separator (12), where the organic solvent is lighter than water. Examples of combinations of this type, where the organic phases in (5), (8) and (12) are of lower specific gravity than the corresponding aqueous phases, are perisobutyric acid in benzene, peracetic acid in ethyl acetate and perpropionic acid in diisopropyl ether or in benzene. Combinations where the organic phase in the process is in every case of higher specific gravity than the corresponding aqueous phases arise when using tetrachloroethylene with the corresponding percarboxylic acids. In the case of the combination of perpropionic acid and dichloropropane (as the organic solvent), the 1,2-dichloropropane in process stage (b) constitutes the light phase, given the sulphuric acid and $H_2O_2$ concentrations prevailing in the aqueous phase of (b), whilst in stage (c) the solution of perpropionic acid in dichloropropane represents the heavy phase when the water wash is being carried out. An expert can very satisfactorily estimate, from the physical data of the mixtures and of the pure compounds, whether the organic solution of the percarboxylic acid arises as the light or heavy phase in the individual process stages. Furthermore, such effects are of no importance as regards the successful execution of the process according to the invention; they merely require, at times, that the apparatuses be connected up in the opposite manner. In this context it should be expressly pointed out, with regard to the arrangement of the apparatus, that it is also possible to integrate the extraction unit (8) into the extraction unit (5) which is used for process step (b). When extraction columns are used, this can be done by mounting the apparatus (8) on top of the extraction column (5), thereby producing a single column, in the upper part of which, between theoretical separation stage n and theoretical separation stage n+10, process step (c) can then be carried out. In general, however, it is more advantageous, especially if water is employed for the wash according to (c), to use a battery of mixer-separators which comprises the appropriate number of theoretical separation stages, since then, in most cases, the stream (13), which may have been divided up, can be introduced in a more defined manner than is generally possible with industrial extraction columns equipped with trays.

The extracts coming from process step (b) (in FIG. 1, the stream (7)), for which the process is suitable, contain 5 to 50% by weight of percarboxylic acid. This percarboxylic acid, alongside the organic solvent, constitutes the greater part of the solution (7). However, it is also possible to employ extracts in which the carboxylic acid content is greater than the percarboxylic acid content. For example, it is possible to use an extract (7) which contains about 20% by weight of propionic acid and about 15% by weight of perpropionic acid. In general, the concentration of percarboxylic acid and carboxylic acid in the extract follows from the reaction or conversion conditions chosen in stage (a) and from the amount of organic solvent employed in step (b). The content of impurities to be removed from (7), such as water, $H_2O_2$ and acid catalyst, depends on several parameters. Firstly, the concentration of strong acid selected for stage (a) plays a role. In addition, the amount of organic solvent relative to the reaction mixture (4) is of importance, as is the $H_2O_2$ content or water content in this product stream leaving the reaction system (3).

In general, the process according to the invention employs extracts, issuing from (5), which contain 0.1 to 5% by weight of water, 0.1 to 3% of hydrogen peroxide and 0.05 to 2% by weight of acid catalyst, such as, for example, sulphuric acid. Of course, it is also possible to employ extracts in which, for example, the content of strong acid is already less than 0.05% by weight, for example 0.03% by weight, whilst the content of $H_2O_2$ on the other hand is greater than 3% by weight. The amount of organic solvent which is recycled from (12) to stage (c) or (b) is 10–70% by weight of the amount of organic solvent which is present in stream (7), namely the extract containing the impurities.

With some combinations of percarboxylic acid and organic solvent it is of advantage not to add the entire amount of organic solvent, recycled after step (c), to the unit (8) upstream of the first theoretical separation stage, but to introduce a part of this amount into the extraction unit (8) at a point which is downstream of the first and upstream of the last theoretical separation stage.

Thus, for example it is advantageous (for instance in the system of perisobutyric acid/benzene), when using four mixer-separators as the extraction unit, (8), if about 30% of the amount recycled to (8) is introduced upstream of the third mixer, whilst the remaining 70% are added to the extract (7) before entry into the first mixer-separator unit.

The water which arises in (12) alongside the organic solvent, and which is recycled to the extraction unit (8) via (16), can contain up to 10% by weight, preferably up to 5% by weight, of percarboxylic acid and up to 5% by weight, preferably not more than 2% by weight, of hydrogen peroxide. Advantageously, a stabilizer, such as, for example, a sodium salt of phosphoric acid or pyrophosphoric acid, is added to this stream before it enters the unit (8).

The amount of wash solution required for process step (c) can vary within wide limits relative to the amount of extract (7) or relative to the total organic phases entering (8), such as stream (13a), (15) and (7). The amount is, for example, relative to extract (7), 0.1-10, preferably 0.3-5, particularly preferentially 0.5 to 3, % by volume of water or of an aqueous solution. However, with a view to an economical design of the overall process it is necessary to keep the total amounts of water introduced into process stage (c) as low as possible. This, however, has to be balanced with the requirements imposed by the need to remove the amounts of $H_2O_2$ and acid catalyst contained in extract (7) as extensively as possible.

The advantage of the process according to the invention compared to known processes is firstly that, viewed in absolute terms, that is to say relative to the amount of percarboxylic acid isolated with stream (21) as a pure organic solution, the proportion of water or aqueous solution which must be employed for stage (c) can be reduced, whilst at the same time the back-wash action, that is to say the removal of the impurities such as $H_2O_2$ and strong acid, becomes better, that is to say the concentrations of these compounds in the stream (21) are—for a comparable percarboxylic acid content—ultimately lower. This is all the more surprising since it would have been assumed that, as a result of the dilution—resulting from the recycling of the organic solvent—of the extract (7) which is to be washed, a poorer washing action would result even if the amount of wash water was the same.

A further advantage which is not insignificant when carrying out the process according to the invention industrially resides in the fact that the energy requirement for process step (d) can be reduced substantially, since the proportions of water and organic solvent to be evaporated in unit (9) are, viewed overall, lower than in known processes, for example in the process of German Auslegeschrift No. 2,519,289 or of German Offenlegungsschrift No. 2,519,298.

The stream (18) which leaves the unit (8; stage c), and which is an aqueous solution in which the $H_2O_2$ washed out from (7) and the proportions of acid catalyst which were present in (7) are contained, additionally contains percarboxylic acid and may also contain the corresponding carboxylic acid as well as small proportions of organic solvent. In general, the solubility of organic solvent in this aqueous phase (18) is 0.5 to 10% by weight. If the stream (18) contains less than 5% by weight of organic solvent, the stream is advantageously recycled to reaction stage (a). However, as already mentioned, stream (18) can also be entirely or partially fed to process stage (b).

The content of water in the organic phase leaving stage (c) (stream (10)) is in general 0.5 to 10% by weight, preferably 1-8% by weight, and very particularly preferentially 1.5-5% by weight. This water content is removed azeotropically in (9) at the top, so that the water content in the bottom product of the distillation unit (9) (stream (21)) is in general less than 1% by weight, preferably less than 0.5% by weight, and particularly preferentially less than 0.2% by weight. However, it is also possible to arrange for lower or higher concentrations of water in the organic solution of the percarboxylic acid (21). Preferably, however, unit (9) is operated in such a way that stream (21) contains less than 0.5% by weight of water.

The pure organic solutions of percarboxylic acids obtained in accordance with the process of the invention in general contain less than 1% by weight of hydrogen peroxide, preferably less than 0.6% by weight and very particularly preferentially less than 0.3% by weight of $H_2O_2$.

The content of strong acid in the pure percarboxylic acid solutions obtained as the bottom product of process step (d) is in general less than 0.1% by weight, preferably less than 0.05% by weight, and very particularly preferentially not more than 0.01% by weight.

A further possible way of carrying out the process according to the invention is to work with a solvent mixture, wherein one of the two solvents, hereafter referred to as the second solvent, passes through process steps (c) and (d) and is taken off at the top of the distillation unit (9), together with the water contained in (10). After this second solvent has once been introduced via line (23) (compare FIG. 1), it serves as a water-entraining agent in step (d) and separates out as the organic phase in (12). Thereafter, it is introduced, in accordance with the invention, into the extraction unit (8) via (13), at the points already mentioned. After having passed through (8), it appears in (10) and the cycle starts afresh, if the process is being carried out continuously.

The second solvent, the so-called auxiliary solvent, should conform to the following requirements: it should have a similar density to that of the solvent used for process step (b). Furthermore, it should have a very low water solubility and should form an azeotrope with water. The boiling point of the auxiliary solvent should if possible be at least 10° C. below the boiling point of the percarboxylic acid and the boiling point of the organic solvent used in (b). It is of course also possible to use a proportion of the auxiliary solvent, recycled via (13), for process step (b) via (22) (compare FIG. 1), in which case step (b) is carried out with a mixture of two solvents. In the system perpropionic acid/tetrachloroethylene, carbon tetrachloride or chloroform have, for example, proved very successful as the auxiliary solvent which passes through stages (8) and (9). Benzene can also be used as the auxiliary solvent in the stated combination of percarboxylic acid and organic solvent.

The operating conditions under which the process steps according to (c) and (d) are carried out are already known. The unit (8) is operated at pressures of 800-1,200 mbar and at temperatures of 10°-40° C. The distillation column (9) is advantageously operated under reduced pressure in order to expose the percarboxylic acid to as little heat as possible. The organic solution of the percarboxylic acid (stream (10)) which is introduced into (9) can have one of the known stabilizers added to it via line (20).

The number of separation stages to be provided in column (9) can be varied within wide limits. It depends, of course, on the particular system of percarboxylic acid/solvent which is employed. In general, a column which has 2-10 theoretical plates for the distillation section and 2-10 theoretical plates for the concentration section is used. For example, a unit (9) which comprises a total of 8 theoretical stages, and where the stream (10) is introduced upstream of the fourth theoretical plate is suitable for the system of perpropionic acid/benzene.

Figure 2:
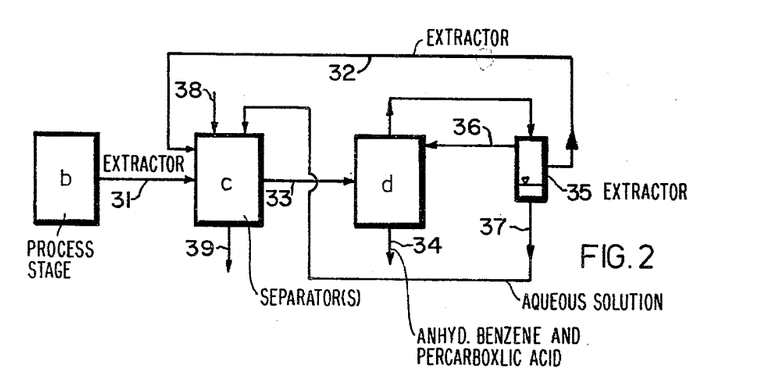
FIG. 2 is a flow diagram showing another variant for preparing a percarboxylic acid in accordance with the process of the present invention.

An embodiment of the process according to the invention will be explained below, for example for the system of perisobutyric acid/benzene, in relation to FIG. 2.

From process stage (b), in continuous operation, about 100–120 parts, per unit time, of a benzene extract are taken off via line (31), the extract containing 30–32% by weight of perisobutyric acid, 9–11% by weight of isobutyric acid, 2–3% by weight of water, about 1% by weight of hydrogen peroxide and 0.4–0.6% by weight of sodium bisulphate. This extract is fed to stage (c), which consists of four mixer-separators operating in countercurrent. Simultaneously with the extract, 28–30 parts of benzene, containing about 1% by weight of perisobutyric acid, are introduced via line (32) into the mixer of the first unit of the mixer-separator battery. Stream (2) is the return stream from process stage (d). A washed benzene solution which is composed of 22–23% by weight of perisobutyric acid, 7–8% by weight of isobutyric acid, 3–4% by weight of water and 0.1–0.2% by weight of $H_2O_2$ is taken from the separator of the fourth extraction stage via (33). The stream (33) is introduced into a distillation column having 5 to 8 theoretical separation stages and operated at 200–500 mbar. From the bottom of this column of process step (d), about 100 parts per unit time of a completely anhydrous benzene solution are taken off via line (34), the solution containing 28–31% by weight of perisobutyric acid in addition to about 10% by weight of isobutyric acid. $NaHSO_4$ is no longer detectable. Only about 0.1% by weight of hydrogen peroxide is still present in this solution.

The distillate container (35) of the said column collects, per unit time, 5–6 parts of an aqueous solution which contains about 1% by weight of perisobutyric acid and small amounts of $H_2O_2$, as well as 58 to 60 parts of benzene, of which about 30 parts are fed, via line (36) as reflux to the top of the column. The remaining benzene is fed to stage (c) via (32), as already mentioned. The aqueous solution arising in (35) is introduced, via line (37), into the mixing device of the fourth mixer-separator, which simultaneously receives via (38), per unit time, 0.5 to 1 part of water which contains small amounts of sodium pyrophosphate. The aqueous solution which issues as the heavy phase from (c) and which in addition to hydrogen peroxide and sodium bisulphate also contains some benzene and perisobutyric acid, is taken off via line (39) and recycled to process step (a).

Figure 3:
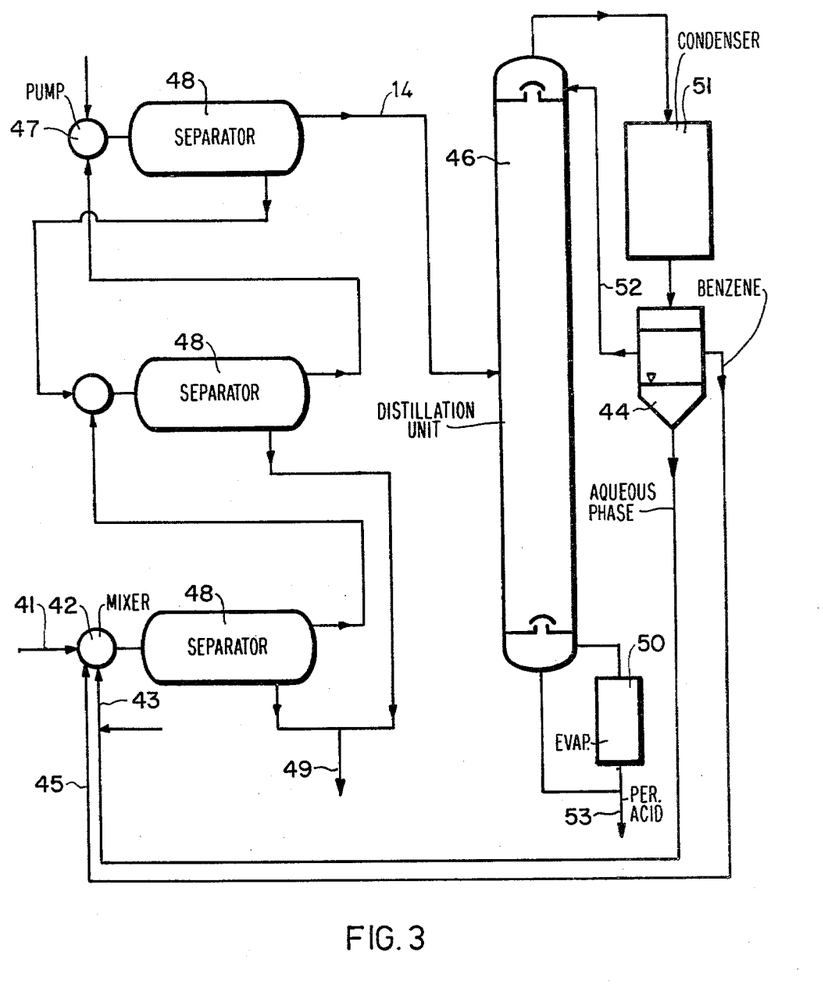
FIG. 3 is a flow diagram showing still another variant for carrying out the process of the invention.

EXAMPLE 1 (FIG. 3)

A solution, obtained by extracting a reaction mixture, consisting of sulphuric acid, hydrogen peroxide, propionic acid and perpropionic acid, with benzene, is fed to a mixer-separator battery via line (41). This extraction system, which is operated at 30° C., comprises three superposed mixer-separators, of which each unit consists of a mixing pump with a downstream separating vessel (48) of about 1.5 liters capacity.

The benzene solution to be treated is fed in an amount of about 2,310 g per hour to the mixing pump (42) of the lower stage (48). This solution contains 22.4% by weight of perpropionic acid and 13.6% by weight of propionic acid, as well as impurities, namely water, hydrogen peroxide and $H_2SO_4$ in respective concentrations of 0.8% by weight, 0.6% by weight and 0.1% by weight. In addition, 90 ml per hour of an aqueous solution are fed to the mixing pump (42) via line (43); this aqueous solution is obtained when the aqueous phase (44) of the top product of the subsequent azeotropic distillation, which is obtained in an amount of 69 ml per hour and in addition to 4% by weight of perpropionic acid contains small amounts of $H_2O_2$, is mixed with 21 ml of water to which minute amounts of sodium pyrophosphate have been added. Furthermore, 822 ml/h of benzene which in addition to traces of water and propionic acid contains about 1.5% by weight of perpropionic acid are introduced into the mixing device (42) via line (45). This benzene is the organic phase of the top product of the distillation unit (46).

The benzene solution of perpropionic acid, which is taken as the light phase from the lower separating vessel (48), passes through the middle mixer-separator arrangement and is then fed, together with 34 ml of water, to the mixing pump (47) belonging to the upper units. The aqueous phase obtained after phase separation has taken place in the upper separator (48) is passed to the middle extraction stage. The aqueous solutions which collect as heavy phases in the middle and lower separating vessel are combined and fed to the reaction system via line (49). Solution (49) contains about 32% by weight of perpropionic acid, 16.7% by weight of propionic acid, 6.5% by weight of $H_2O_2$, 1% by weight of sulphuric acid and small amounts of benzene. It is obtained in an amount of 190 g per hour.

The benzene solution of perpropionic acid which leaves the upper separator (48) is introduced via line (54) into the distillation unit (46). This distillation unit consists of a column of 5 cm diameter, provided with 10 bubble cap trays, a falling film evaporator (50), a condenser (51) and a separator for separating the phases of the distillate. The benzene solution taken from the upper separator (48) is introduced onto the fifth tray. At a pressure of 400 mbar and a temperature, at the top of the column, of 45°–47° C., 69 ml per hour of aqueous phase (44) and 1,274 g of benzene are obtained as the distillate. Of the benzene phase obtained, 625 ml/h are fed as reflux, to the column via line (52), whilst the remainder is fed to the mixing pump (42) via line (45).

As the bottom product of this azeotropic distillation, the pure solution of perpropionic acid in benzene is taken from column (46), via line (53) in an amount of 2,172 g per hour.

This perpropionic acid solution contains 20.73% by weight of PPA ($\triangleq 5$ mols/hr). The water content of the solution is less than 0.05% by weight. The concentration of $H_2O_2$ is 0.1% by weight, whilst the $H_2SO_4$ content is less than 5 ppm.

In order to make clear the advantages of the process according to the invention, the numerical data of example 3 of German Offenlegungsschrift No. 2,519,298 are employed below for comparison, where no recycling of the organic phase of the distillate from the azeotropic column is employed, that is to say where this phase is entirely employed as reflux for the azeotropic column. All data are recalculated on the basis of 5 mols/hr of perpropionic acid, obtained as the bottom product of the distillation unit (46).

For the washing process in the three-stage mixer-separator battery, the following amounts of water or of an aqueous solution are required for 5 mols/hr of obtained solution of perpropionic acid in benzene:

| according to the invention | according to German Offenlegungsschrift 2,519,298 |
|---|---|
| 125 g/hr | 149.2 g/hr |

It will be clear that according to the process of the invention the amount of water used is 16% less, compared with that of German Offenlegungsschrift No. 2,519,298.

The content of free hydrogen peroxide in the benzene solution of perpropionic acid (PPA) is 0.16% by weight in the process of German Offenlegungsschrift No. 2,519,298. This means a loss of $H_2O_2$ of 3.55 g per 5 mols of PPA. In the process according to the invention, this value is only 2.2 g/5 mols of PPA.

The advantageous method of working of the process according to the invention becomes particularly clear if the amounts of water and benzene to be evaporated in the distillation unit (46) are compared. In the process of German Offenlegungsschrift No. 2,519,298 these amounts are 1,740 g/hr of benzene, which passes as reflux to the column, and 94 g/hr of water in each case again related to 5 mols/hr of PPA solution in benzene.

In the process according to the invention, the corresponding values are 1,274 g/hr of benzene (the sum of the stream (5) and (12)) and 68.8 g/hr of water.

Further, it must be regarded as an advantage that the stream (49), which issues as the heavy phase from the mixer-separator battery, could be substantially reduced compared to the method of working of German Offenlegungsschrift No. 2,519,298. This is advantageous inasmuch as the water present in this stream must again be removed at some other point of the process, for example in the unit for reconcentrating the acid catalyst.

Figure 4:
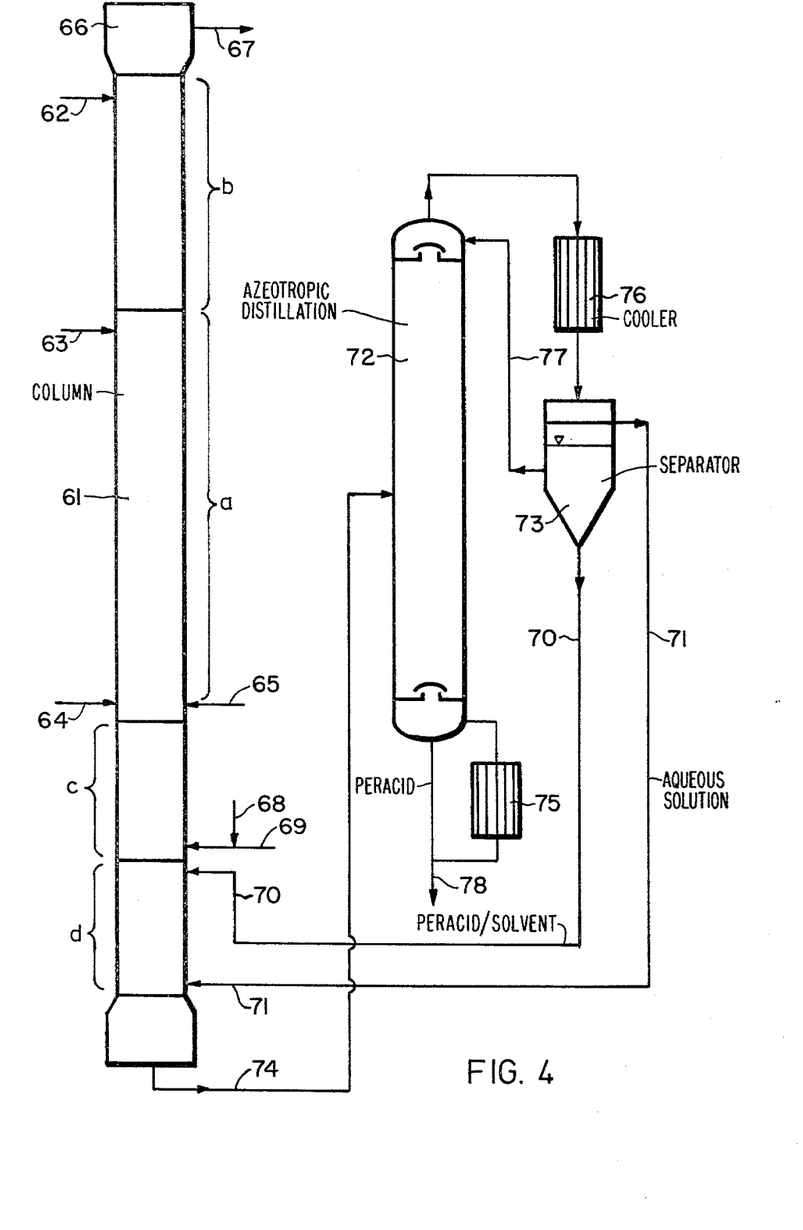
FIG. 4 is a flow diagram similar to FIG. 3 but showing still a further variant for preparing a percarboxylic acid solution in accordance with the invention.

EXAMPLE 2 (FIG. 4)

The reaction of propionic acid with $H_2O_2$, the extraction with tetrachloroethylene and the washing of the extract are carried out simultaneously in the extraction unit (61).

The apparatus (61) consists of a pulsating column of 2.5 cm diameter, provided with 200 sieve trays. About 10 of these trays are provided per meter of height, and the trays have different free cross-sections in accordance with the loading they undergo, which varies with height. The entire apparatus (61) is kept at 30° C. At its upper and lower end it possesses a settling vessel in which the phase separation takes place.

In the zone marked (a), about 9 theoretical separation stages are realised. In this zone, the reaction, and the isolation of the extract, namely a solution of perpropionic acid in tetrachloroethylene, take place. In zone (b), which possesses about 5 theoretical stages, the raffinate which issues from (a) and which is of lower specific gravity than the organic solvent, is treated with fresh tetrachloroethylene in order to remove residual perpropionic acid and propionic acid from the sulphuric acid solution. Zone (b) thus serves for backwashing the aqueous phase, whilst in zone (c) and (d) the treatment of the extract with dilute $H_2SO_4$ and water is carried out. In each of (c) and (d), about 3 theoretical separation stages can be realised.

In an experiment carried out continuously, 188 ml per hour of tetrachloroethylene containing less than 0.2% by weight of propionic acid are introduced into column (61) via line (62). 2.2 kg per hour of a 25% strength by weight solution of propionic acid in tetrachloroethylene are introduced via (63), whilst hydrogen peroxide and sulphuric acid enter the column (61) via (64) and (65). 243 g of $H_2O_2$ in the form of a 70% strength by weight aqueous solution ($\triangleq$ 5 mols/hr of $H_2O_2$) and 280 g of a 75% strength by weight solution of sulphuric acid are employed.

An aqueous solution (483 g per hour), which in addition to 44–45% by weight of sulphuric acid only contains about 3% by weight of $H_2O_2$, is taken off, via line (67), from the separating vessel (66) located at the top of the column.

7 g/hr of 98% strength by weight of $H_2SO_4$ enter column (61) through line (68), and 28 ml/hr of water through line (67).

The streams (70) and (77) are, respectively, recycled carbon tetrachloride, which is employed as an auxiliary solvent for the azeotropic dehydration occurring in unit (72), and recycled aqueous solution taken as the light phase from the separator (73). Stream (10) is an 0.7% strength by weight solution of perpropionic acid in $CCl_4$ and is introduced into the column at at rate of 685 g/hr. Stream (71) is an aqueous solution which in addition to 2.1% by weight of perpropionic acid still contains about 0.8–1.0% by weight of $H_2O_2$. It arises in (73) in an amount of 93 g/hr and is fed in entirely at the base of the column (61).

3.35 kg per hour of a 12.3% strength by weight solution of perpropionic acid are taken from column (61) via (74) and are fed to the downstream distillation unit (72).

Column (72) is provided with 9 bubble cap trays and has a diameter of 5 cm. Heating is effected by means of the heat exchanger (75), whilst the cooler (76) serves to condense the products which leave the top. The column (72) is operated under a pressure of 480 mbar. The temperature at the top is 47°–49° C. Stream (74) is introduced above the fifth tray.

After condensation of the top vapours, the separator (73) collects, per hour, 93 g of the aqueous phase and a total of about 1,355 ml of $CCl_4$. Of this amount of carbon tetrachloride, the amount already mentioned is taken off through line (70) and recycled to the extraction column (61), whilst the remainder is introduced into the column (72) as reflux, via line (77).

From the bottom of the column (72), 2,575 g per hour of a 15.7% strength by weight solution of perpropionic acid in tetrachloroethylene are discharged via line (78). This solution no longer contains any water and any sulphuric acid. The concentration of propionic acid is 8.4% by weight. The content of free hydrogen peroxide is less than 0.1% by weight.

What is claimed is:

1. In a process for the continuous preparation of a pure organic solution of a percarboxylic acid having 2 to 5 carbon atoms, which comprises
   (a) contacting aqueous hydrogen peroxide with a carboxylic acid containing 2 to 5 carbon atoms in the presence of an acid catalyst at a feed molar ratio of H₂O₂ to carboxylic acid of 0.5:1 to 30:1, (b) isolating an extract essentially containing the percarboxylic acid and the corresponding carboxylic acid not converted in stage (a), by extracting the reaction mixture obtained according to stage (a) with an organic solvent, (c) extracting the extract with water or an aqueous solution substantially free of hydrogen peroxide and mineral acid in an extraction unit provided with one to ten theoretical separation stages whereby to obtain an aqueous extract, and (d) dehydrating the solution of the percarboxylic acid and organic solvent obtained according to (c), by azeotropic distillation to obtain a top product, condensing the top product and separating the resultant condensate into an organic phase and an aqueous phase, the improvement wherein the organic phase of the top product of the azeotropic distillation, obtained during the dehydration according to (d), is entirely or partially directly recycled to stage (c) and/or entirely or partially directly recycled to stage (b).

2. A process according to claim 1 wherein the organic phase of the top product of the azeotropic distillation is entirely recycled to stage (c).

3. A process according to claim 1 wherein the organic phase of the top product of the azeotropic distillation is partially recycled to stage (c).

4. A process according to claim 1 wherein the organic phase of the top product of the azeotropic distillation is entirely recycled to stage (b).

5. A process according to claim 1 wherein the organic phase of the top product of the azeotropic distillation is partially recycled to stage (b).

6. A process according to claim 1 wherein the entire amount or portion of the organic phase of the top product of the azeotropic distillation is recycled to stage (c) upstream of the first theoretical separation stage.

7. A process according to claim 1 wherein the entire amount of portion of the organic phase of the top product of the azeotropic distillation is fed to the extraction unit at a point downstream of the first and upstream of the last theoretical separation stage.

8. A process according to claim 1 wherein the organic phase of the top product of the azeotropic distillation is fed at least in part to stage (d) and said organic phase consists essentially of an organic solvent having a boiling point under normal pressure of about 30° to 140° C.

9. A process according to claim 1 wherein the organic phase of the top product of the azeotropic distillation of stage (d) consists essentially of an organic solvent which is capable of forming a azeotrope with water, the boiling point of which is at least 10° C. below the boiling point of the percarboxylic acid.

10. A process according to claim 1 wherein the organic phase of the top product of the azeotropic distillation of stage (d) consists essentially of a solvent which is an aromatic hydrocarbon having 6 to 10 carbon atoms, an aliphatic or cycloaliphatic hydrocarbon containing 5 to 12 carbon atoms, a chloro hydrocarbon containing 1 to 10 carbon atoms and 1 to 4 chlorine atoms, an ester of a carboxylic acid containing 1 to 5 carbon atoms with a straight-chain or branched alcohol containing 1 to 8 carbon atoms or an ether containing 2 to 10 carbon atoms.

11. A process according to claim 1 wherein the organic phase from stage (d) is divided up, for purposes of recycle, such that the amount recycled to stage (d) is 5 to 70 percent of the amount which is recycled to stage (c) and a portion of such organic phase is recycled to stage (b) and a portion is recycled to stage (c).

12. A process according to claim 1 wherein the amount of the organic phase of the top product of the azeotropic distillation which is recycled is 10 to 70 percent by weight of the amount of solvent present in the extract obtained in stage (b) and fed to stage (c).

13. A process according to claim 1 wherein said carboxylic acid is acetic acid, propionic acid, n-butyric acid or isobutyric acid.

14. A process according to claim 1 wherein the process is conducted such that there is obtained a solution of a percarboxylic acid in an organic solvent which contains less than 0.5 percent by weight water, less than 0.6 percent by weight hydrogen peroxide and less than 0.05 percent by weight of acid catalyst.

15. A process according to claim 1 wherein the aqueous extract obtained in stage (c) is recycled partially or entirely to the extraction according to stage (b) or entirely or partially to the reactions according to stage (a).

* * * * *